United States Patent [19]

Tackney et al.

[11] Patent Number: 5,334,532

[45] Date of Patent: Aug. 2, 1994

[54] PDGF-B FUSION PROTEIN, VECTORS, AND HOST CELLS FOR USE IN PRODUCTION THEREOF

[75] Inventors: Charles Tackney, Brooklyn, N.Y.; Jurgen Hoppe, Wurzburg, Fed. Rep. of Germany; Wolfram Eichner; Herbert Weich, both of Braunschweig, Fed. Rep. of Germany

[73] Assignee: ImClone Systems Incorporated, New York, N.Y.

[21] Appl. No.: 675,885

[22] Filed: Jun. 4, 1991

[30] Foreign Application Priority Data

Oct. 6, 1988 [DE] Fed. Rep. of Germany ....... 3834079

[51] Int. Cl.[5] ............. C12N 15/00; C12N 5/00; C07K 13/00
[52] U.S. Cl. .................. 435/252.33; 435/69.7; 435/320.1; 530/350; 530/399
[58] Field of Search .......... 435/69.1, 69.4, 69.7, 435/71.2, 172.3, 252.33, 320.1; 536/27; 530/399, 350

[56] References Cited

U.S. PATENT DOCUMENTS

| | | | |
|---|---|---|---|
| 4,738,921 | 4/1988 | Belagaje et al. | 435/68 |
| 4,751,180 | 6/1988 | Cousens et al. | 435/68 |
| 4,766,073 | 8/1988 | Murray et al. | 435/69.4 |
| 4,769,328 | 9/1988 | Murray et al. | 435/69.1 |
| 4,845,075 | 7/1989 | Murray et al. | 514/12 |
| 4,849,407 | 7/1989 | Murray et al. | 514/12 |
| 5,128,321 | 7/1992 | Murray et al. | 514/12 |

OTHER PUBLICATIONS

Hoppe, J. et al., *Biochemistry*, 28:2956–2960, 1989, Apr.
Wang, J. et al., *J. Biol. Chem.*, 259(17): 10645–48, 1984.
Devare, S. et al., *Cell*, 36:43–49, 1984.
Hannink, M. et al., *Mol. Cell. Biol.*, 6(4): 1343–1348, 1986.
Stanley, K. K. et al., *Embo Journal*, 3(6): 1429–34, 1984.

*Primary Examiner*—Robert J. Hill, Jr.
*Assistant Examiner*—Marianne Porta Allen
*Attorney, Agent, or Firm*—Irving N. Feit; Eric J. Sheets

[57] ABSTRACT

The present invention provides a method for production of recombinant PDGF-B in prokaryotic cells. Also provided are DNA constructs for fusion protein useful in the production of the biologically active product.

3 Claims, 10 Drawing Sheets

Figure 2

```
1          10         20         30         40         50         60
SLGSLTIAE  PAMIAECKTR TEVFEISRRL IDRTNANFLV WPPCVEVQRC SGCCNNRNVQC
              IAECKTR TEVFEISRRL IDRTNANFLV WPPCVEVQRC SGCCNNRNVQC 70         80         90        100        110
RPTQVQLRP  VQVRKIEIVR KKPIFKKATV TLEDHLACKC ETVAAARPVT
RPTQVQLRP  VQVRKIEIVR KKPIFKKATV TLEDHLACKC ETVAAARPVT RSPLN
```

Figure 3A

```
5' CGCAAGGGATAAATATCTAACACCGTGCGTGTTGACTATTTTACCTCTGGCGGTGATAAT 3'
        10        20        30        40        50        60

M  E  Q  R  I  T  L  K  E  A  W  D
5' GGTTGCATGTACTAAGGAGGTTGTATGGAACAACGCATAACCCTGAAAGAAGCTTGGGAT 3'
        70        80        90       100       110       120

R  S  G  A  W  L  L  F  V  S  L  V  K  R  K  T  T  L  A  P
5' CGATCCGGAGCTTGGCTGTTGCCCGTCTCACTGGTGAAAAGAAAAACCACCCTGGCGCCC 3'
       130       140       150       160       170       180

N  T  Q  T  A  S  P  R  A  L  A  D  S  L  M  Q  L  A  R  Q
5' AATACGCAAACCGCCTCTCCCCGCGCGTTGGCCGATTCATTAATGCAGCTGGCACGACAG 3'
       190       200       210       220       230       240

V  S  R  L  N  R  L  A  A  H  P  P  F  A  S  W  R  N  S  E
5' GTTTCCCGACTTAATCGCCTTGCAGCACATCCCCCTTTCGCCAGCTGGCGTAATAGCGAA 3'
       250       260       270       280       290       300

E  A  R  T  D  R  P  S  Q  Q  L  R  S  L  N  G  E  W  R  F
5' GAGGCCCGCACCGATCGCCCTTCCCAACAGTTGCGCAGCCTGAATGGCGAATGGCGCTTT 3'
       310       320       330       340       350       360

A  W  F  P  A  P  E  A  V  P  E  S  W  L  E  C  D  L  P  E
5' GCCTGGTTTCCGGCACCAGAAGCGGTGCCGGAAAGCTGGCTGGAGTGCGATCTTCCTGAG 3'
       370       380       390       400       410       420

A  D  T  V  V  V  P  S  N  W  Q  M  H  G  Y  D  A  P  I  Y
5' GCCGATACTGTCGTCGTCCCCTCAAACTGGCAGATGCACGGTTACGATGCGCCCATCTAC 3'
       430       440       450       460       470       480

T  N  V  T  Y  P  I  T  V  N  P  P  F  V  P  T  E  N  P  T
5' ACCAACGTAACCTATCCCATTACGGTCAATCCGCCGTTTGTTCCCACGGAGAATCCGACG 3'
       490       500       510       520       530       540

G  C  Y  S  L  T  F  N  V  D  E  S  W  L  Q  E  G  Q  T  R
5' GGTTGTTACTCGCTCACATTTAATGTTGATGAAAGCTGGCTACAGGAAGGCCAGACGCGA 3'
       550       560       570       580       590       600

I  I  F  D  G  V  N  S  A  F  H  L  W  C  N  G  R  W  V  G
5' ATTATTTTTGATGGCGTTAACTCGGCGTTTCATCTGTGGTGCAACGGGCGCTGGGTCGGT 3'
       610       620       630       640       650       660
```

Figure 3B

```
       Y   G   Q   D   S   R   L   P   S   E   F   D   L   S   A   F   L   R   A   G
5' TACGGCCAGGACAGTCGTTTGCCGTCTGAATTTGACCTGAGCGCATTTTTACGCGCCGGA 3'
         670         680         690         700         710         720

E   N   R   L   A   V   M   V   L   R   W   S   D   G   S   Y   L   E   D   Q
5' GAAAACCGCCTCGCGGTGATGGTGCTGCGTTGGAGTGACGGCAGTTATCTGGAAGATCAG 3'
         730         740         750         760         770         780

D   M   W   R   M   S   G   I   F   R   D   V   S   L   L   H   K   P   T   T
5' GATATGTGGCGGATGAGCGGCATTTTCCGTGACGTCTCGTTGCTGCATAAACCGACTACA 3'
         790         800         810         820         830         840

Q   I   S   D   F   H   V   A   T   R   F   N   D   D   F   S   R   A   V   L
5' CAAATCAGCGATTTCCATGTTGCCACTCGCTTTAATGATGATTTCAGCCGCGCTGTACTG 3'
         850         860         870         880         890         900

E   A   E   V   Q   M   C   G   E   L   R   D   Y   L   R   V   T   V   S   L
5' GAGGCTGAAGTTCAGATGTGCGGCGAGTTGCGTGACTACCTACGGGTAACAGTTTCTTTA 3'
         910         920         930         940         950         960

W   Q   G   E   T   Q   V   A   S   G   T   A   P   F   G   G   E   I   I   D
5' TGGCAGGGTGAAACGCAGGTCGCCAGCGGCACCGCGCCTTTCGGCGGTGAAATTATCGAT 3'
         970         980         990        1000        1010        1020

E   R   G   G   Y   A   D   R   V   T   L   R   L   N   V   E   N   P   K   L
5' GAGCGTGGTGGTTATGCCGATCGCGTCACACTACGTCTGAACGTCGAAAACCCGAAACTG 3'
        1030        1040        1050        1060        1070        1080

W   S   A   E   I   P   N   L   Y   R   A   V   V   E   L   H   T   A   D   G
5' TGGAGCGCCGAAATCCCGAATCTCTATCGTGCGGTGGTTGAACTGCACACCGCCGACGGC 3'
        1090        1100        1110        1120        1130        1140

T   L   I   E   A   E   A   C   D   V   G   F   R   E   V   R   I   E   N   G
5' ACGCTGATTGAAGCAGAAGCCTGCGATGTCGGTTTCCGCGAGGTGCGGATTGAAAATGGT 3'
        1150        1160        1170        1180        1190        1200

L   L   L   L   N   G   K   P   L   L   I   R   G   V   N   R   H   E   H   H
5' CTGCTGCTGCTGAACGGCAAGCCGTTGCTGATTCGAGGCGTTAACCGTCACGAGCATCAT 3'
        1210        1220        1230        1240        1250        1260

P   L   H   G   Q   V   M   D   E   Q   T   M   V   Q   D   P   L   G   S   L
5' CCTCTGCATGGTCAGGTCATGGATGAGCAGACGATGGTGCAGGATCCCCTGGGTTCCCTG 3'
        1270        1280        1290        1300        1310        1320

T   I   A   E   P   A   M   I   A   E   C   K   T   R   T   E   V   F   E   I
5' ACCATTGCTGAGCCGGCCATGATCGCCGAGTGCAAGACGCGCACCGAGGTGTTCGAGATC 3'
        1330        1340        1350        1360        1370        1380

S   R   R   L   I   D   R   T   N   A   N   F   L   V   W   P   P   C   V   E
5' TCCCGGCGCCTCATAGACCGCACCAACGCCAACTTCCTGGTGTGGCCGCCCTGTGTGGAG 3'
        1390        1400        1410        1420        1430        1440
```

Figure 3c

```
      V  Q  R  C  S  G  C  C  N  N  R  N  V  Q  C  R  P  T  Q  V
5' GTGCAGCGCTGCTCCGGCTGCTGCAACAACCGCAACGTGCAGTGCCGCCCCACCCAGGTG 3'
       1450      1460      1470      1480      1490      1500

Q  L  R  P  V  Q  V  R  K  I  E  I  V  R  K  K  P  I  F  K
5' CAGCTGCGACCTGTCCAGGTGAGAAAGATCGAGATTGTGCGGAAGAAGCCAATCTTTAAG 3'
       1510      1520      1530      1540      1550      1560

K  A  T  V  T  L  E  D  H  L  A  C  K  C  E  T  V  A  A  A
5' AAGGCCACGGTGACGCTGGAAGACCACCTGGCATGCAAGTGTGAGACAGTGGCAGCTGCA 3'
       1570      1580      1590      1600      1610      1620

R  P  V  T  R  S  P  L  N
5' CGGCCTGTGACCCGAAGCCCGCTTAATTAATTACGGGTACCGAGCTCGAATTCGTCGACC 3'
       1630      1640      1650      1660      1670      1680

5' TGCAGCCAAGCTTGCTGATTGATTGACCGGATCGATCCGGCTCTAGAATTAATTCACCTC 3'
       1690      1700      1710      1720      1730      1740

5' GAAAGCAAGCTGATAAACCGATACAATTAAAGGCTCCTTTTGGAGCCTTTTTTTTTGGAG 3'
       1750      1760      1770      1780      1790      1800

5' ATTTTCAACGTGAAAAAATTATTATTCGCAATTCAAGCTAATTCACCTAGAAAGCAAGCT 3'
       1810      1820      1830      1840      1850      1860

5' GATAAACCGATACAATTAAAGGCTCCTTTTGGAGCCTTTTTTTTGGAGATTTTCAACGT 3'
       1870      1880      1890      1900      1910      1920

5' GAAAAAATTATTATTCGCAATTCAAGCTCTGCCTCGCGCGTTTCGGTGATGACGGTGAAA 3'
       1930      1940      1950      1960      1970      1980

5' ACCTCTGACACATGCAGCTCCCGGAGACGGTCACAGCTTGTCTGTAAGCGGATGCCGGGA 3'
       1990      2000      2010      2020      2030      2040

5' GCAGACAAGCCCGTCAGGGCGCGTCAGCGGGTGTTGGCGGGTGTCGGGGCGCAGCCATGA 3'
       2050      2060      2070      2080      2090      2100

5' CCCAGTCACGTAGCGATAGCGGAGTGTATACTGGCTTAACTATGCGGCATCAGAGCAGAT 3'
       2110      2120      2130      2140      2150      2160

5' TGTACTGAGAGTGCACCATATGCGGTGTGAAATACCGCACAGATGCGTAAGGAGAAAATA 3'
       2170      2180      2190      2200      2210      2220

5' CCGCATCAGGCGCTCTTCCGCTTCCTCGCTCACTGACTCGCTGCGCTCGGTCGTTCGGCT 3'
       2230      2240      2250      2260      2270      2280

5' GCGGCGAGCGGTATCAGCTCACTCAAAGGCGGTAATACGGTTATCCACAGAATCAGGGGA 3'
       2290      2300      2310      2320      2330      2340
```

Figure 3D

5' TAACGCAGGAAAGAACATGTGAGCAAAAGGCCAGCAAAAGGCCAGGAACCGTAAAAAGGC 3'
      2350      2360      2370      2380      2390      2400

5' CGCGTTGCTGGCGTTTTTCCATAGGCTCCGCCCCCCTGACGAGCATCACAAAAATCGACG 3'
      2410      2420      2430      2440      2450      2460

5' CTCAAGTCAGAGGTGGCGAAACCCGACAGGACTATAAAGATACCAGGCGTTTCCCCCTGG 3'
      2470      2480      2490      2500      2510      2520

5' AAGCTCCCTCGTGCGCTCTCCTGTTCCGACCCTGCCGCTTACCGGATACCTGTCCGCCTT 3'
      2530      2540      2550      2560      2570      2580

5' TCTCCCTTCGGGAAGCGTGGCGCTTTCTCAATGCTCACGCTGTAGGTATCTCAGTTCGGT 3'
      2590      2600      2610      2620      2630      2640

5' GTAGGTCGTTCGCTCCAAGCTGGGCTGTGTGCACGAACCCCCCGTTCAGCCCGACCGCTG 3'
      2650      2660      2670      2680      2690      2700

5' CGCCTTATCCGGTAACTATCGTCTTGAGTCCAACCCGGTAAGACACGACTTATCGCCACT 3'
      2710      2720      2730      2740      2750      2760

5' GGCAGCAGCCACTGGTAACAGGATTAGCAGAGCGAGGTATGTAGGCGGTGCTACAGAGTT 3'
      2770      2780      2790      2800      2810      2820

5' CTTGAAGTGGTGGCCTAACTACGGCTACACTAGAAGGACAGTATTTGGTATCTGCGCTCT 3'
      2830      2840      2850      2860      2870      2880

5' GCTGAAGCCAGTTACCTTCGGAAAAAGAGTTGGTAGCTCTTGATCCGGCAAACAAACCAC 3'
      2890      2900      2910      2920      2930      2940

5' CGCTGGTAGCGGTGGTTTTTTTGTTTGCAAGCAGCAGATTACGCGCAGAAAAAAAGGATC 3'
      2950      2960      2970      2980      2990      3000

5' TCAAGAAGATCCTTTGATCTTTTCTACGGGGTCTGACGCTCAGTGGAACGAAAACTCACG 3'
      3010      3020      3030      3040      3050      3060

5' TTAAGGGATTTTGGTCATGAGATTATCAAAAAGGATCTTCACCTAGATCCTTTTAAATTA 3'
      3070      3080      3090      3100      3110      3120

5' AAAATGAAGTTTTAAATCAATCTAAAGTATATATGAGTAAACTTGGTCTGACAGTTACCA 3'
      3130      3140      3150      3160      3170      3180

5' ATGCTTAATCAGTGAGGCACCTATCTCAGCGATCTGTCTATTTCGTTCATCCATAGTTGC 3'
      3190      3200      3210      3220      3230      3240

5' CTGACTCCCCGTCGTGTAGATAACTACGATACGGGAGGGCTTACCATCTGGCCCCAGTGC 3'
      3250      3260      3270      3280      3290      3300

Figure 3E

5' TGCAATGATA̱CCGCGAGACC̱CACGCTCACC̱GGCTCCAGAṮTTATCAGCAA̱TAAACCAGCC̱ 3'
     3310        3320        3330        3340        3350        3360

5' AGCCGGAAGG̱GCCGAGCGCA̱GAAGTGGTCC̱TGCAACTTTA̱TCCGCCTCCA̱TCCAGTCTAṮ 3'
     3370        3380        3390        3400        3410        3420

5' TAATTGTTGC̱CGGGAAGCTA̱GAGTAAGTAG̱TTCGCCAGTṮAATAGTTTGC̱GCAACGTTGṮ 3'
     3430        3440        3450        3460        3470        3480

5' TGCCATTGCṮACAGGCATCG̱TGGTGTCACG̱CTCGTCGTTṮGGTATGGCTṮCATTCAGCTC̱ 3'
     3490        3500        3510        3520        3530        3540

5' CGGTTCCCAA̱CGATCAAGGC̱GAGTTACATG̱ATCCCCATGṮTGTGCAAAAA̱AGCGGTTAG̱ 3'
     3550        3560        3570        3580        3590        3600

5' CTCCTTCGGṮCCTCCGATCG̱TTGTCAGAAG̱TAAGTTGGCC̱GCAGTGTTAṮCACTCATGGṮ 3'
     3610        3620        3630        3640        3650        3660

5' TATGGCAGCA̱CTGCATAATṮCTCTTACTGṮCATGCCATCC̱GTAAGATGCṮTTTCTGTGAC̱ 3'
     3670        3680        3690        3700        3710        3720

5' TGGTGAGTAC̱TCAACCAAGṮCATTCTGAGA̱ATAGTGTATG̱CGGCGACCGA̱GTTGCTCTTG̱ 3'
     3730        3740        3750        3760        3770        3780

5' CCCGGCGTCA̱ATACGGGATA̱ATACCGCGCC̱ACATAGCAGA̱ACTTTAAAAG̱TGCTCATCAṮ 3'
     3790        3800        3810        3820        3830        3840

5' TGGAAAACGṮTCTTCGGGGC̱GAAAACTCTC̱AAGGATCTTA̱CCGCTGTTGA̱GATCCAGTTC̱ 3'
     3850        3860        3870        3880        3890        3900

5' GATGTAACCC̱ACTCGTGCAC̱CCAACTGATC̱TTCAGCATCṮTTTACTTTCA̱CCAGCGTTTC̱ 3'
     3910        3920        3930        3940        3950        3960

5' TGGGTGAGCA̱AAAACAGGAA̱GGCAAAATGC̱CGCAAAAAAG̱GGAATAAGGG̱CGACACGGAA̱ 3'
     3970        3980        3990        4000        4010        4020

5' ATGTTGAATA̱CTCATACTCṮTCCTTTTTCA̱ATATTATTGA̱AGCATTTATC̱AGGGTTATTG̱ 3'
     4030        4040        4050        4060        4070        4080

5' TCTCATGAGC̱GGATACATAṮTTGAATGTAṮTTAGAAAAAṮAAACAATAGG̱GGTTCCGCG̱ 3'
     4090        4100        4110        4120        4130        4140

5' CACATTTCCC̱CGAAAAGTGC̱CACCTGACGṮCTAAGAAACC̱ATTATTATCA̱TGACATTAAC̱ 3'
     4150        4160        4170        4180        4190        4200

5' CTATAAAATA̱GGCGTATCAC̱GAGGCCCTTṮCGTCTTCAAG̱AATTAATT 3'
     4210        4220        4230        4240

PDGF-B FUSION PROTEIN, VECTORS, AND HOST CELLS FOR USE IN PRODUCTION THEREOF

FIELD OF THE INVENTION

The present invention relates to DNA constructs and methods for producing platelets derived growth factor (PDGF). In particular, the invention relates to DNA constructs encoding a fusion protein containing the PDGF-B sequence, which construct permits the expression of PDGF-B in large quantities by bacterial cells.

BACKGROUND OF THE INVENTION

Cellular Growth Factors Generally

In recent years, significant attention has been paid to the large number of mitogenic factors, more commonly referred to generically as cellular growth factors, which have been found to be produced by various types of human cells. The outstanding characteristic common to these growth factors is their ability to stimulate proliferation in vitro of a number of cell types. In their normal state, diploid cells in culture rely on the presence of exogenous growth factors to initiate division, and in the absence of these factors, cells will leave the cell cycle and remain in $G_1/G_0$ until stimulated externally. On the other hand, transformed cells (e.g., cancerous cells) do not rely upon exogenous growth factors to stimulate mitosis, but rather appear to have some internal control mechanism which permits continuous cell division without any external stimulus. It is in this regard that the so-called "growth factors" have been actively studied. A significant body of evidence suggests that these mitogens may play a role as "transforming proteins" which in vivo are associated with causing the loss of control over growth exhibited by tumor cells. In fact, a number of observations indicate that certain growth factors are routinely made and released by certain human tumor cells in vitro.

Specific Growth Factors

Certain "families" of growth factors have been defined, primarily grouped by their structural similarity. (Helden and Westermark, *Cell* 37:9-20, 1984). Epidermal growth factor (EGF) and certain transforming growth factors (e.g., TGF-α) are relatively low molecular weight (6,000-7,000) single chain proteins which may be natural products of the cellular genome. The insulin family of growth factors, including insulin and insulin-like growth factors (IGFs) are also small proteins sharing sequence homology, Of particular interest to the present invention is the platelet-derived growth factor (PDGF). PDGF is a growth factor, stored in α-platelets, which is released upon platelet activation. Platelets play an integral role in the mechanism of blood clotting, and their activation is initiated by various factors, such as tissue trauma, damage to the endothelial surface of the vascular wall, or trauma to some of the intrinsic clotting factors in the blood. Platelets adhere to the broken surface of blood vessels, and release PDGF. PDGF acts as a potent mitogen which stimulates the production of connective tissue cells generally and of the fibroblasts and smooth muscle necessary to initiate tissue repair; it also acts as a chemoattractant for neutrophils, which are also essential in the wound healing process. Thus, PDGF has been targeted a potential candidate for incorporation into pharmaceutical preparations to be used in vivo for treatment of wounds.

PDGF in purified form is a cationic glycoprotein having a molecular weight of about 30,000. Size heterogeneity is observed, however and this is believed to be the result of varying levels of glycosylation, processing by the cell, and the presence of two forms, PDGF-A and -B. The biologically active form of PDGF is apparently a heterodimer comprising two different polypeptide chains of 14,000 molecular weight linked together by disulfide bridges. PDGF achieves its activity by binding to cell surface receptors. The physiological changes which result from this binding include receptor autophosphorylation and phosphorylation of tyrosine residues of certain cytoplasmic substrates. Its action has been said to be inhibited by $Ca^+$ channel blockers in vascular smooth muscle cells. (Block et al., *PNAS USA* 86:2388-2392, 1989.)

As noted above, there has been considerable speculation that certain growth factors may act as transforming proteins in stimulating proliferation of cells. Interestingly, while the A and B chains of PDGF do share some sequence homology, the B chain in particular is nearly completely homologous with a portion of the amino acid sequence of $p28^{v-sis}$, the transformed product of simian sarcoma virus (SSV; Doolittle et al., *Science* 221:275-276, 1983). Unlike the human native PDGF, however, $p28^{v-sis}$ forms a homodimer, but which is further processed to a size similar to that of PDGF (Robbins et al., *EMBO J* 4:1783-1792, 1985). Indeed, a number of homodimers of A-A and B--B have been reported to have full biological activity. For example, a PDGF-like mitogen, osteosarcoma cell derived growth factor, is an A-chain homodimer (Heldin et al., *Nature* 319:511-514, 1986). Porcine platelets also appear to produce a B-B homodimer (Stroobant et al., *EMBO J* 3:2963-2967, 1984).

Numerous attempts have been made to produce highly purified biologically active PDGF, and many have tried to express recombinant PDGF in various host systems. U.S. Pat. No. 4,479,896, describes a method for isolation and recovery of native PDGF from platelets by method utilizing gel electrophoresis and staining to localize the protein. U.S. Pat. Nos. 4,766,073; 4,769,328; and 4,849,407 each disclose various PDGF analogs which are produced recombinantly in eukaryotic cells, particularly in yeast. European Patent Publication 282 317 discloses purified PDGF B-chain, and monoclonal antibodies useful in the isolation of the B-chain. European Patent Publication 288 307 describes expression vectors the DNA of which encode the human PDGF A-chain as well as expression of the DNA in east and mammalian cells.

Although there has been some success in the production of recombinant PDGF, these results have been achieved primarily in eukaryotic cells, such as yeast and mammalian cells. Although reasonable quantities of product can apparently be produced in such systems, these cells, particularly mammalian cells, can be difficult and expensive to culture, and, therefore, they are not commercially preferred. It is generally preferable to be able to produce recombinant proteins in prokaryotic cells, as these are easily and cheaply produced in large quantities. However, to date, there has been little success in producing PDGF in prokaryotes, in particular *E. coli*. In fact, yield of PDGF in *E. coli* has been extremely difficult to detect and/or the resulting products are typically inactive. It is not clear why production of mature PDGF by *E. coli* has been so poor, but it has been suggested that the processing steps required to produce the functional eukaryote protein cannot be accomplished by a prokaryote, so that the protein may not be folded correctly and the disulfide bridges may not form properly (Devare et al., *Cell* 36:43–49, 1984; Wang et al., *J. Biol. Chem.* 259:10645–10648, 1984). In order for PDGF to be produced on a commercially useful scale, then, an alternate method of production is necessary. The present invention provides methods and DNA constructs which are useful in producing large quantities of biologically active PDGF-B from *E. coli*.

SUMMARY OF THE INVENTION

The present invention provides a method for producing a biologically active PDGF-B in a prokaryotic cell which comprises:

(i) transforming a prokaryotic host cell with a recombinant gene comprising a nucleotide sequence which encodes a fusion protein, the fusion protein having (a) a segment which is all or part of a prokaryotic protein which is capable of expression by the host cell; (b) a segment having a chemically clearable site; and (c) a segment which is a PDGF-B monomer; the segments of the gene encoding the segments of the fusion protein being operably linked, and capable of expression as a fusion protein by the host cell;

(ii) recovering fusion proteins produced by the host cell;

(iii) chemically cleaving the fusion protein to release the PDGF monomer; and (iv) purifying the monomer.

The monomeric form of PDGF may in some cases exhibit biological activity without further processing. However, in most cases, it will be preferred to reconstitute the dimeric form. Thus, the invention also provides a method for production of a dimeric PDGF, this method encompasses the steps (i)–(iv) above, but in addition, includes the steps of (v) dimerizing the monomer by forming disulfide bridges; and (vi) recovering a PDGF homodimer.

This method provides quantities of PDGF in *E. coli* of as much as 30% of the total cell protein produced.

The method also provides a recombinant gene encoding the fusion protein capable of yielding PDGF biological activity, as well as vectors containing these recombinant genes. In addition, transformed prokaryotic cell lines containing the recombinant gene, which cell lines are capable of producing large quantities of PDGF monomer.

The methods, genes, vectors and cell lines of the present invention enable the production of large quantities of biologically active PDGF-B, at a cost which is realistic for commercial exploitation.

BRIEF DESCRIPTION OF THE FIGURES

FIG. 2 illustrates the amino acid sequence of native PDGF-B and the sequence of recombinant PDGF-B recovered by CNBr cleavage of the fusion protein encoded by plasmid pE-pF14. It is noted that the first 12 amino acids are removed by cleavage with CNBr in rPDGF-B. Furthermore, rPDGF-B additionally contains 5 amino acids at the C terminus. Three of these amino acids differ from PDGF-BB sequences and originate from the stop linker at the SmaI junction (see FIG. 1).

FIG. 3A–E illustrates the entire nucleotide sequence of the plasmid pE-pF14, including the sequence of PDGF-B.

FIG. 4 illustrates the results of SDS polyacrylamide gel electrophoresis of:

A) lysates from *E. coli* cells;
B) monomeric S-sulfonated rPDGF-B;
C) rPDGF-BB after denaturing;
D) purified rPDGF-B (dimer); and
S) standard.

Figure 5:
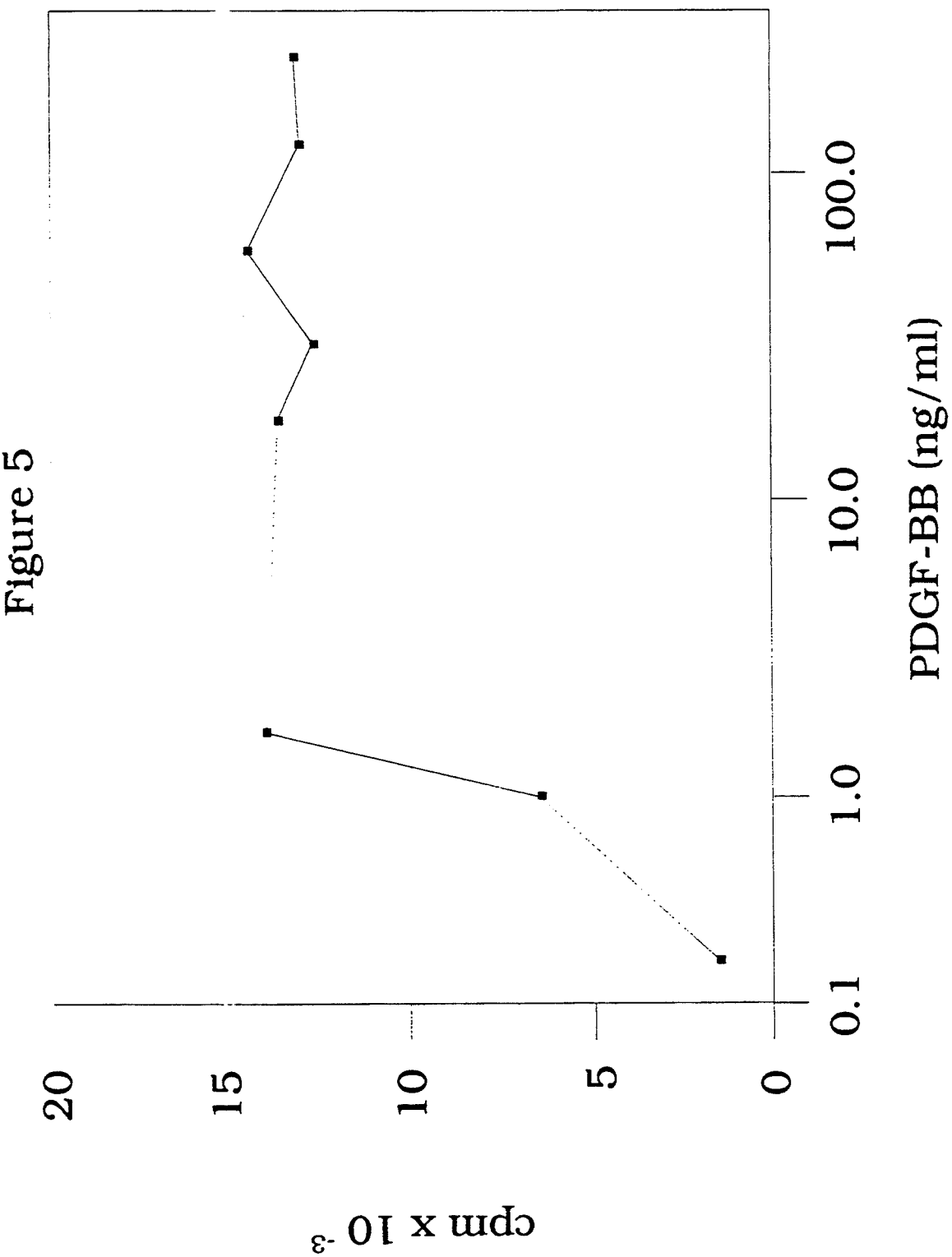

FIG. 5 illustrates the biological activity of the recombinant PDGF-BB produced by the present method. The graph illustrates the stimulation of uptake of $^3$H-thymidine in initially quiescent AKR-28 fibroblasts.

Figure 6:
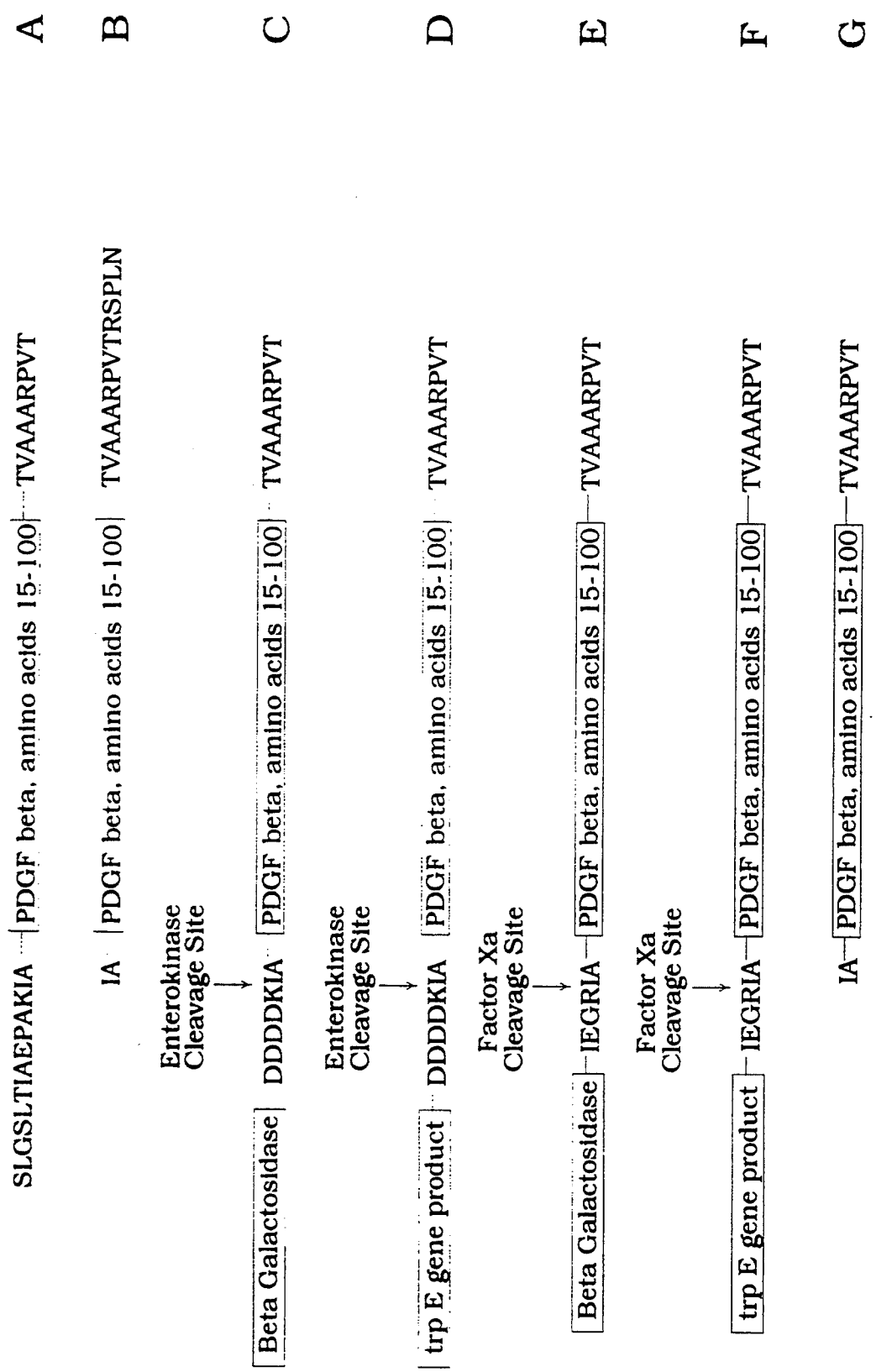

FIG. 6 illustrates a number of schematic representations of fusion proteins of the present invention.

A. Naturally processed human PDGF-B monomeric form.

B. Protein produced in accordance with the present examples following cyanogen bromide cleavage, with 12 amino acids missing at the amino terminus, and a five carboxy terminal extension.

C. $\beta$-gal - PDGF-B fusion protein modified to have a natural carboxy terminus and an enterokinase cleavage site to yield amino terminus as in B.

D. As in C, but as a trp E fusion.

E. As in C, but with a Factor $X_a$ cleavage site.

F. As in D, but with a Factor $X_a$ cleavage site.

Product of cleavage of fusions C, D, E, and F with appropriate proteolytic enzyme.

DETAILED DESCRIPTION OF THE INVENTION

Fusion Protein Sequence

Fusion proteins have been known to be used for expression of eukaryotic proteins, to place the gene for desired protein under the control of a strong promoter, and/or to confer a detectable signal to an otherwise difficult to identify protein. However, the results of the expression are not predictable a priori, and fusion proteins comprising PDGF have never been made or suggested. The usual situation is one in which the amino terminus of the fusion protein is encoded by a prokaryotic sequence, which can be placed under the control of a promoter and the carboxy terminus is encoded by the eukaryotic sequence.

In the present case, it has been found that PDGF can be produced in unexpectedly high yield in a prokaryotic host by the use of a fusion protein for expression, and that a biologically active dimer can be readily created from the monomers so produced. The fundamental portions of the DNA sequence which produce the fusion protein are (a) a segment which represents at least a portion of a prokaryotic protein capable of expression by the host cell; (b) a segment which encodes an amino acid sequence having a chemically cleavable site; and (c) a segment which encodes a protein which either has PDGF biological activity per se, or which possesses PDGF biological activity when in dimeric form. Additionally, the fusion protein sequences must be operably linked to each other and to the appropriate control elements so that the gene may be transcribed, translated and expressed by the host organism of choice. These features are discussed in more detail below.

Prokaryotic Protein Segment

It is typical in the production of fusion proteins generally to use as the prokaryotic protein a sequence which produces detectable enzymatic activity, and preferably one which has a visually detectable enzymatic function. The most frequently used enzyme for this purpose is $\beta$-galactosidase. In order to readily identify clones which have been transformed, the putative transformants can be screened for the presence of $\beta$-galactosidase activity (Miller, *Experiments in Molecular Genetics*, Cold Spring Harbor Press, N.Y. 1972). The production of color in this assay is indicative of the production of the fusion protein by the host cell, and intensity of color is an indication of the relative expression of the fusion protein. However, this is not the sole method by which a fusion protein-producing clone can be identified.

In the course of the construction of the gene for the fusion protein described in the present examples, a SalI/EcoRV digestion of the plasmid pEx-1 lead to a deletion of over 1000 nucleotides, or almost two-thirds of the protein. Nonetheless, the high level of expression of the cro-$\beta$-gal fusion protein was still achieved. Thus, the incorporation of the complete sequence coding for the prokaryotic protein is not required to achieve the desired level of expression, although it may be desirable from the point of view of detectability. Identification of a clone producing a cro-$\beta$-gal PDGF-B--fusion protein is facilitated by the fact that only one long reading frame exits in the PDGF-B gene which will lead to a significant inclose in the cro-$\beta$-gal protein. Thus, clones are easily isolated, showing a molecular weight increased by 14,000.

In the embodiment described in the present examples, the amino terminal portion of the fusion protein sequence is the cro repressor-$\beta$-galactosidase gene (cro-$\beta$-gal) or a portion thereof. However, the present method is not limited by the use of this particular sequence. For example, an alternate prokaryotic protein is the trpE gene product (Kleid et al., *Science* 214:1125–1129, 1981), as demonstrated in FIG. 5.

Chemically Cleavable Site

In order to be able to remove the prokaryotic sequence from the PDGF sequence after isolation of the fusion protein to facilitate purification of PDGF, the DNA sequence encoding the fusion protein should contain between the prokayotic sequence and the functional PDGF sequence, a sequence which codes for a chemically clearable site. As used throughout the specification and claims, "chemically clearable site" means one that can be treated with a chemical reagent to break the peptide bonds at the site, thereby effectively separating the enzyme sequence from the PDGF sequence. This function can be implemented in a number of ways. For example, in the present examples, cyanogen bromide is used to cleave at the methionine which occurs at position 12 of the native PDGF amino acid sequence. Although this results in the deletion of the first 12 amino acids of the PDGF sequence, the remaining portion of the protein still exhibits a very high level of PDGF biological activity.

In an alternate embodiment, however, it may be preferred to retain the entire PDGF sequence. In such a case, a fusion protein gene may be constructed which contains a linking sequence between the enzyme sequence and the PDGF sequence. The linker DNA sequence may encode a peptide sequence which is susceptible to degradation by proteolytic enzyme. The specific sequence used is not critical, provided that the enzyme to be employed will not also attack a site within the critical portion of PDGF sequence as well. Some preferred enzymes to be used for this purpose are enterokinase or Factor Xa, each of which cleave specific sites, the sequences of which are depicted in FIG. 5. However, any other protease-susceptible sequence may also be employed, provided that the sequence is not one which is repeated within a critical portion of the PDGF-B sequence itself. It is within the ability of one skilled in the art to choose alternate clearable sites, given knowledge of an enzyme's site of action.

PDGF Sequence

The sequence of native PDGF-B is well known and reproduced in FIG. 2. The appropriate sequence can also be isolated from a human cDNA library derived from an appropriate cell source. The PDGF-B fragments of the library can be identified readily by hybridization with all or a portion of the V-sis (SSV) gene, which is substantially homologous to the PDGF-B chain. Identity of the isolated cDNA with the PDGF-B chain can be verified by DNA sequencing. It should be understood, however, that the scope of the invention is not limited to the use of the entire native PDGF sequence. As has already been shown above, the removal of the first 12 amino acids in the native sequence had substantially no effect on the biological activity. Moreover, as will be seen from the subsequent examples, the addition of several amino acids to the natural end of the molecule also does not adversely affect the activity of protein. Thus, it is clear that substantial modification can be made to the sequence of the PDGF without losing activity. It is therefore contemplated that the phrase "biologically active PDGF" encompass both the native sequence and homologues thereof, the sequence of which may differ from the native sequence, but which is sufficiently duplicative to retain the necessary activity. The types of changes which may be made in the sequence, for example, are "silent" or "conservative" changes which retain the essential structure of the molecule. In other words, alterations of the native nucleotide sequence by deletions, additions, or substitutions of different nucleotide residues resulting in a gene sequence that encodes the same, or a functionally equivalent, gene product are contemplated. The gene product may contain deletions, additions, or substitutions of amino acid residues. Substitutions may be made on the basis of similarity in polarity, charge, solubility, hydrophobicity, hydrophilicity and/or the amphipathic nature of the residues involved. For example, negatively charged amino acids include aspattic acid and glutamic acid; positively charged amino acids include lysine and arginine; amino acids with uncharged polar head groups or nonpolar head groups have similar hydrophilicity values include the following: leucine, isoleucine, valine; glycine, alanine; asparagine, glutamine; serine, threonine; phenylalanine, tyrosine. Those skilled in the art will recognize the types of changes which are feasible and which will produce a functional PDGF molecule.

In the present examples, an embodiment is described in which the PDGF portion of the fusion protein lacks the first 12 amino acids of the native sequence, due to the cyanogen bromide cleavage used to release the monomer. This is in conformity with previous reports that regions encoding amino-terminal prosequences of the sis gene can be deleted without adversely affecting the ability of the proteins to form dimers and to transform a host. (Richter-King et al., *PNAS USA* 82:5295–5299, 1985; Hannink et al., *Mol. Cell Biol.* 6:1343–1348, 1986; Sauer et al., *J. Virol.* 59:292–300, 1986). Additionally, the exemplified rPDGF-B has a C-terminal extension of five residues, due to the deletion of the original stop codon by SmaI digestion, and insertion of a stop linker at this site. However, the fusion protein may also be prepared with the PDGF-B sequence in its natural state.

From this information, it is clear that the PDGF sequence may be modified substantially at both the N- and C-termini and still retain biological activity; thus, fusion proteins containing either the native sequence, or a sequence which has been reduced or extended at either end are encompassed within the scope of the term "PDGF monomer" as used in the present specification and claims. It is also contemplated that the renatured dimeric PDGF may be comprised of monomers of different lengths.

Purification

To obtain the isolated PDGF-B chains, the transformed host cells are grown under the culture conditions appropriate for the species. Depending on the species used, the protein may be isolated from both the supernatant and the cells, per se; however, with *E. coli*, it is necessary to extract the protein directly from the cells. Inclusion bodies can be isolated from the cells according to the method described by Stanley and Luzio, supra and the protein isolated therefrom. The fusion protein is then cleaved to release the monomer by a method appropriate for the specific cleavage site built into the protein.

Once the monomer has been released, further purification can be achieved. In the presence of a low pH environment, it will generally be preferable to reversibly protect the thiol groups of the B-chain from oxidation prior to any additional steps. Protection of the thiol groups can be achieved by sulfonation. This may be accomplished by addition to the protein of a sulfite and dithionite. Certain other methods, however, such as chromatography in the presence of mercaptoethanol or modification of thiols by DTNB, did not produce a useful assembled product.

Gel permeation chromatography is a preferred method of further purification of the recombinant protein, normally in the presence of a denaturing agent, e.g. guanidine hydrochloride, having a molarity of about 1–6. Any fusion protein fragments remaining after cleavage are readily removed by this process. After dialysis against water, a precipitate appears in which some amount of nonprotein material may remain after the filtration, but the peptides are further isolated by extraction with formic acid. The peptides may then be further purified by HPLC.

Although the foregoing methods represent preferred embodiments, it must be noted that the PDGF may be isolated by any appropriate chromatographic method. Variations on these methods will be readily recognized by one skilled in the art.

Renaturation

As noted above, there may be some instances in which a PDGF-B monomer exhibits biological activity. However, in order to reliably obtain biological activity, the rPDGF-B is preferably renatured to its dimeric form; dimerization does not appear to occur spontaneously. In order to achieve renaturation, the sulfo groups on the purified and protected monomers are reduced, and disulfide bridges formed. Normally, this can be accomplished in a single step, for example, in the presence of urea (up to 4 M and thiol reagents. For example, renaturation is rather easily achieved by treatment of the purified protein with glutathione (up to 100 hiM), or 2-mercaptoethanol (up to a concentration of 2%), followed by incubation at room temperature for up to 2 days. The dimerization under these conditions occurs rather specifically, and in high yield. The dimer thus formed can be further purified by reversed-phase chromatography or ion-exchange chromatography. This is evidenced by the appearance of a band of about $M_r$ 24,000 which comprises about 20% of the total protein mass. Few, if any, higher molecular weight forms appear. The yield was 0.7–1.0 mg of rPDGF-BB from 1 liter of culture. This compares most favorably with the expression rate of PDGF dimers in eukaryotic systems, which in some cases may be as low as 5–20 ng/ml (Kelly et al., *EMBO J* 4:3399–3405, 1984) a level which is unacceptable for commercial production of PDGF.

Biological Activity

Renatured PDGF prepared according to the present method has excellent growth promoting activity when tested in vitro. In fact, rPDGF stimulated [$^3$H]-thymidine incorporation into AKR-2B fibroblasts in a concentration range of from 1–3 ng/ml (50% activation), whereas PDGF purified from platelets was slightly less active (1.5–4 ng/ml). Moreover, both products stimulated [$^3$H]-thymidine incorporation to the same maximum- Thus, rPDGF-BB is qualitatively comparable with PDGF derived from human platelets. (See FIG. 4).

Control Elements and Vectors

In order to obtain effective expression of the fusion protein gene, appropriate control elements must be selected. Generally, the choice will be made in accordance with the chosen cloning vector. In order to achieve transcription and translation of the inserted gene, the gene must be placed under the control of a promoter compatible with the host cell.

A promoter is a region of DNA at which RNA polymerase attaches and initiates transcription. The prmoter selected may be any one which has been isolated from the host cell organism. For example, *E. coli*, a commonly used host system, has numerous promoters such as the lac or recA promoter associated with it, its bacteriophages or its plasmids. Also, synthetic or recombinantly produced promoters, such as the λ phage $P_L$ and $P_R$ promoters may be used to direct high level production of the segments of DNA adjacent to it.

An initiation signal is also necessary in order to attain efficient transcription and translation of the gene. For example, in *E. coli*, mRNA, a ribosome binding site includes the translational start codon (AUG or GUG) and another sequence complementary to the bases of the 3' end of 16S ribosomal RNA. Several of these latter sequences (Shine-Dalgarno or S-D) have been identified in *E. coli* and other suitable host cell types. Any SD-ATG sequence which is compatible with the host cell system, can be employed. These include, but are not limited to, the cro gene or N gene of coliphage lambda, or the *E. coli* tryptophan E, D, C, B or A genes.

A number of methods exist for the insertion of DNA fragments into cloning vectors in vitro. DNA ligase is an enzyme which seals single-stranded nicks between adjacent nucleotides in a duplex DNA chain; this enzyme may therefore be used to covalently join the annealed cohesive ends produced by certain restriction enzymes. Alternately, DNA ligase can be used to catalyze the formation of phosphodiester bonds between blunt-ended fragments. Finally, the enzyme terminal deoxynucleotidyl transferase may be employed to form homopolymeric 3'-single-stranded tails at the ends of fragments; by addition of oligo (dA) sequences to the 3' end of one population, and oligo (dT) blocks to 3' ends of a second population, the two types of molecules can anneal to form dimeric circles. Any of these methods may be used to ligate the gene segment promoter and other control elements into specific sites in the vector. Thus, the gene coding for the fusion protein is ligated into the chosen vector in a specific relationship to the vector promoter and control elements, so that the sequence is in the correct reading frame with respect to the vector ATG sequence. The method employed may be any of the known expression vectors or their derivatives; among the most frequently used are plasmid vectors such as pBR 322, pAC 105, pVA 5, pACYC 177, PKH 47, pACYC 184, pUB 110, pmB9, pBR325, Col El, pSC101, pBR313, pML21, RSF2124, pCRi or RP4; bacteriophage vectors such as lambda gtll lambda gt-WES-lambdaB, Charon 28, Charon 4A, lambda gt-1-lambda BC, lambda-gt-1-lambda B, M13mp7, M13mpS, and M13mp9.

In the embodiment described in the present examples, the expression vector employed is a derivative of the pEX plasmid family (Stanley and Luzio, *EMBO J.* 3:2963–2967, 1984), which was used to transform *E. coli*, specifically strain NF1. This combination is preferred because of the substantial quantities of PDGF-B which are obtainable from *E. coli*, i.e. as much as 30% of the total cell protein. However, given the variety of expression vectors available which are compatible with a number of different host cell types, including other *E. coli* strains, it is well within the ability of one skilled in the art to combine an alternate expression vector with a different prokaryotic host cell line. Among other preferred host cell lines are, for example, *E. coli* HB101, JM109, RR-1, or DH-1.

6. EXAMPLES

Materials and Methods

The following is a list of materials employed in the present examples, and the sources or references from which they were obtained.

| | |
|---|---|
| *E. coli* JM103 | Pharmacia |
| *E. coli* NF1 | EMBO J 3:1429–1434 (1984) |
| pEX1 (plasmid) | Genofit Heidelberg; also EMBO J 3:1429–1434 (1984) |

| | |
|---|---|
| M13mp18 (vector) | Pharmacia; also FEBS Letters 198:344–348, 345 (1986) |
| pJLA504 (plasmid) | Gene 52:279–283, 280 (1987) |
| pMVW-2 (plasmid) | FEBS Letters 198:344–348, 346 (1986) |

Guanidine hydrochloride and Tris were from Sigma, formic acid, 2-propanol, acetonitrile and trifluoroacetic acid from Merck, Sephacryl S-200 from Pharmacia, the Si-300-polyolbutyl chromatography column and ampicillin from Serra, medium and supplements from Gibco, and radiochemicals from Amersham.

Growth stimulating activity was determined by the method of Shipley et al *Cancer Res.* 44:710–716 (1984). Purified PDGF was prepared from fresh platelets essentially as described in Johnson et al. (*Biochem. Biophys. Res. Commun.* 104:66–74, 1982).

Gel electrophoresis was performed as described (Hoppe et al., *Eur. J. Biochem.* 155:259–264, 1986; 13.5 percent gels). Amino acid analyses were determined by Biotronic's Analyzer I C2000. Amino-terminal sequence analyses were performed with the L12 (Sequemat) solid phase sequenator. For that purpose the protein was bound by its amino groups to glass activated with diisothiocyanate (Hoppe et al., supra). Alternatively, sequences were determined by the 470A gas phase analyzer (Applied Biosystems). The protein content was determined by the methods of Bradford (*Anal. Biochem.* 72:248–253, 1976)) and Redinbaugh & Turley (*Anal. Biochem.* 153:267–271, 1986).

Construction of an Expression Vector

Figure 1:
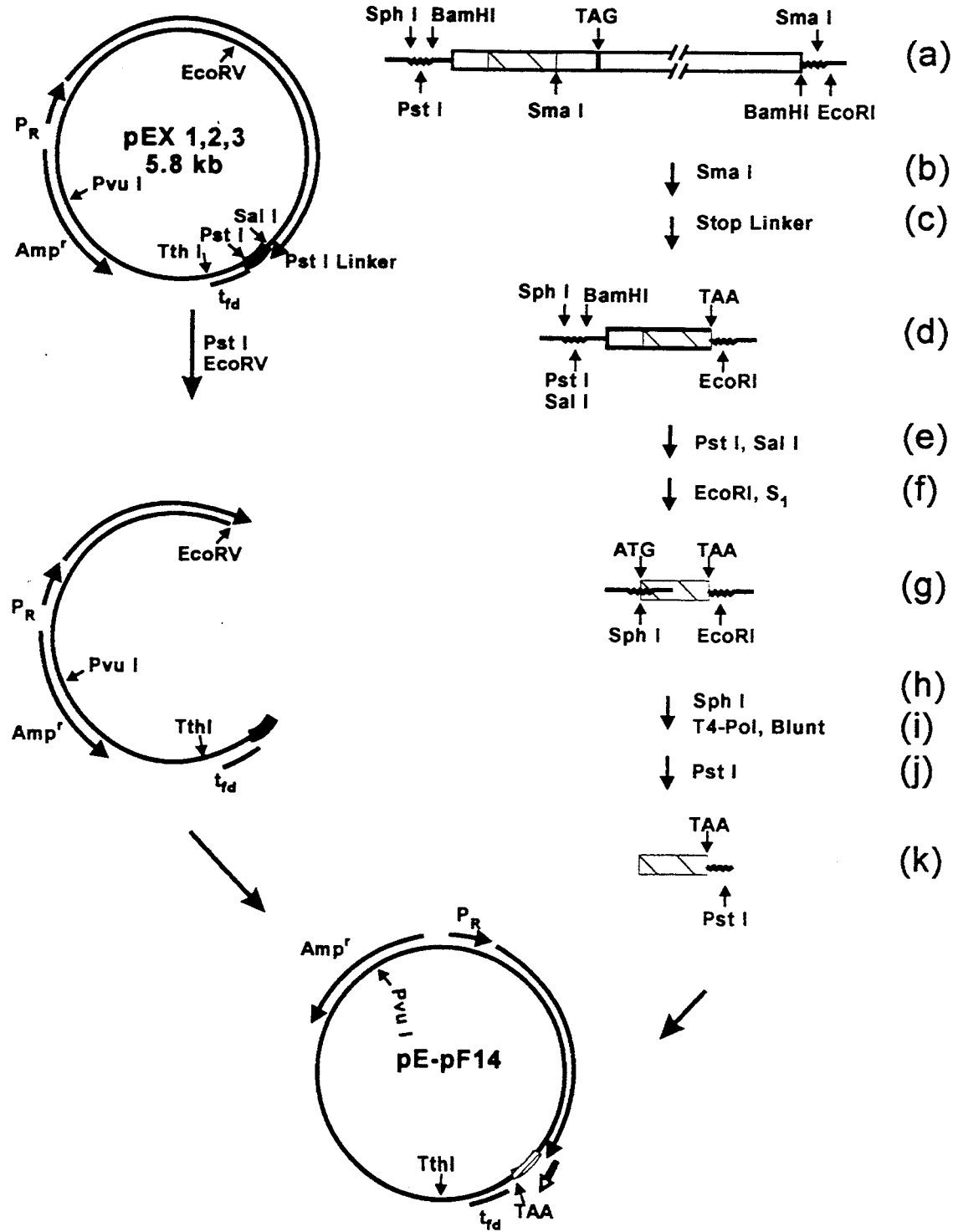
FIG. 1 illustrates the strategy for construction of plasmid pE-PF14. The 2 kb long BamHI fragment obtained from the plasmid pMWV-2 has been integrated in reversed orientation into the phages M-3mp18 (open boxes: c-cis-mRNA sequences, hatched boxes: regions for mature PDGF-B). The long 3' range, which includes the original stop codon TAG, was removed by SmaI digestion. A stop linker was introduced into this region. 5' regions were removed by exonuclease-III digestion. After one passage through the vector pJLA504, PDGF-B coding sequences in the read pattern were integrated into the SalI/EcoRV points of vector pEX1. $P_R$=bacteriophage promoter; cro'-lac7=cro-$\beta$-galactosidase fusion protein; tfd=phage transcription terminator.

The strain NF1 was used as host (K12 delta-H1 delta trp lac Z-am), which has integrated the defective lambda prophage (Nam7Nam53cI 857 delta-H1) (Stanley & Luzio, supra). The starting material was the c-sis-containing BamHI DNA fragment (2 kb) from the clone pMVW-2 (Weich et al., *FEBS Lett.* 198:344–348, 1986). This fragment was subcloned in the reverse direction into the BamHI junction of the vector M13mp18. By digestion with SmaI (FIG. 1, line b), 3' sequences, which are not translated, and sequences which code for C terminal prosequences, were removed. Then a translation-stop linker (PL Biochemicals) was integrated into this SmaI junction (FIG. 1, line C). To eliminate the 5' encoding region of the c-sis gene, the plasmid was digested with PstI and SalI (FIG. 1, line e) to create 5' and 3' sticky ends for exonuclease III digestion (FIG. 1, line f) as described by Henikoff (*Gene* 28:351–359, 1984). The remaining second strand was removed with $S_1$ nuclease (FIG. 1, line f). By DNA polymerase-I-Klenow fragment treatment smooth ends were produced, and then the plasmid was recycliized by ligase treatment. After transformation into *E. coli* strain JM103, colonies were obtained. The degree of abbreviation by exonuclease-III was determined by miniplasmid preparation and sequencing the plasmid DNA of these colonies. A plasmid was obtained which contained an ATP start codon from the SphI junction from the "multicloning site" of the M13mp18 vector the read pattern with the PDGF-B sequence. The result was a slight change in the $NH_2$ terminus (met-pro-leu-gly instead of ser-leu-gly). The PDGF-B coding sequences were excised by partial SphI/EcoRI digestion and integrated (SphI/EcoRI) in plasmid pJLA 504 (Schauder et al., *Gene* 52:279–283, 1987) to produce an SalI a 3' end. This plasmid was again partially digested with Sph (FIG. 1, line h). Projecting 3′ ends were removed by T4 polymerase treatment (FIG. 1, line i)- A fragment of 390 bp which contained the PDGF-B sequences was isolated after SalI digestion (FIG. 1, line j) and integrated into the SalI/EcoRV locations of the pExl vector (FIG. 1, bottom center).

By the SalI/EcoRV digestion of the plasmid pExl, 1097 nucleotides were removed, which code for about two-thirds of the β-galactosidase. This deletion did not change the high expression of the cro-β-gal fusion protein.

For the identification of clones which efficiently express the PDGF-B sequences, colonies which were obtained after transformation to the strain NF1 were cultivated at 30° C. to an optical density of 0.3 ODU (440 nm) and after that were cultivated for another 3 hours at 42° C. to induce the production of the cro-β-gal fusion proteins. Cells were lysed by ultrasound treatment and dissolved by sodium dodecyl sulfate (SDS) and 2-mercaptoethanol. After polyacrylamide gel electrophoresis in the presence of sodium dodecyl sulfate, an intense band with a molecular weight of 65,000 d (instead of 48,000) occurred in numerous preparations, indicating the expression of PDGF sequences. The isolated plasmid was named pE-pF14. An *E. coli* strain NF1 transformed with the pE-pF14 plasmid has been deposited with the ATCC., and assigned accession number 68104.

Cultivation of Cells and Preparation of Inclusion Bodies

*E. coli* cells were cultivated in LB medium with 50 to 100 μm/ml of ampicillin in one-liter cultures at 30° C. to an optical density of 0.2 ODU (440 nm) and then shaken at 42° C. for another 3 hours. The cells were harvested by centrifugation (5000 ×g. 10 min) and suspended in 20 ml of tris-HC1 (20 riM) and EDTA (0.5 mM) of pH 7.8. For a typical preparation, 20 to 30 liters of culture were grown. The cells were opened up by two passes through a Ribi press (Sorvall) at 20,000 psi. The fusion protein consisting of parts of the cro repressor and the β-galactosidase plus PDGF-B (recombinant monomeric growth factor from type B thrombocytes) formed inclusion bodies which were obtained by centrifugation (6000 ×g, 10 min) after the addition of 2% Triton X-100 (e concentration).

Reduction and CNBr Cleavage

Inclusion bodies from 20 to 30 liters of culture were dissolved in 100 ml of Tris-HC1 (50 mM; pH 7.8) with 2% SDS (sodium dodecyl sulfate) and 2% 2-mercaptoethanol) (approx. 1 hour, 37° C.). Small amounts of insoluble matter were removed by centrifugation 20,000 ×g in 30 minutes. 2 volumes of acetone were added to the supernatant liquor at 0° C. After 15 minutes at 0° C. a precipitate was centrifuged off (6000 ×g 10 min) which was dissolved in 80 ml of formic acid (100%). Then 20 ml H$_2$O was added insoluble matter was removed at 50,000 ×g in 1 hour. One gram of CNBr and 200 μl of 2-mercaptoethanol were added; the reaction mixture was left overnight at room temperature. The solution was dried on the rotary evaporator. The residue was dissolved with 80 ml of 6 M guanidine hydrochloride and the pH was adjusted to 7.5 by adding 30% NaOH.

It is to be noted that PDGF-B has only one methionine residue in position 12 in the NH$_2$ terminal part of the mature sequence. Cleavage of the cro-β-gal-PDGF-B fusion protein at the methionine residue with CNBr therefore yielded fragments shortened by 12 amino acids. Furthermore, the introduction of the stop signal resulted in alterations of the protein at the C terminus (FIG. 2).

S-Sulfonation

One gram of Na$_2$SO$_3$ and 0.25 g of Na$_2$S$_2$O$_6$ were added to the solution obtained. The mixture was let stand at room temperature for 5 hours. Insoluble matter was removed by centrifugation (50,000 g, 1 h).

Purification of S-Sulfonated Monomeric rPDGF-B

For gel filtration, the solution obtained above was applied to a column (size 5 cm diam. ×100 cm) which was filled with Sephacryl S200. The eluent was 4 M of guanidine hydrochloride with 50 mM Tris-HC1 of pH 7.4. The rate of flow was 160 ml/h. Fractions 15 ml were collected. Aliquots of the fractions were analyzed by SDS gel electrophoresis, and fractions having proteins with a molecular weight of approximately 14 kd were combined and dialyzed overnight against 5 liters of water. During the dialysis a precipitate formed which could be largely dissolved by the addition of formic acid to an end concentration of 10%. Insoluble matter was removed by centrifugation (20,000 ×g, 20 min). The supernatant liquor (approx. 160 ml) was applied to HPLC column (2 cm diam.×25 cm; reversed phase: Si-300 polyol butyl, 5 μm, Serra) at a flow rate of 2.5 ml/min. After the application of the sample, the column was washed with approximately twice its capacity. rPDGF-B monomer was eluted by a linear gradient of 10% formic acid/H$_2$O against 10% formic acid, 60% 2-propanol and 30% H$_2$O for 180 min at a flow rate of 2.5 ml/min. rPDGF-B eluted at about 40 to 60 min. Corresponding fractions were combined and dialyzed against 5 liters H$_2$O.

Dimerization and Purification

S-sulfonated monomeric rPDGF-B was adjusted to a concentration of 0.4 mg/ml. Then urea was added to an end concentration of 1 M, then glutathione (5 mM) and oxidized glutathione (0.5 mM). The pH was adjusted to 7.8 by the addition of Tris-HC1 (Tris base in some cases) to 7.8 (end concentration about 50 mM), and the reaction mixture was let stand for 2 days at room temperature. Dimeric rPDGF-BB was purified by ion exchange chromatography. For this purpose about 20 mg of protein was put through a 1 ml column of S-sepharose in 20 mM of Tris-HC1 (pH 7.4). Monomeric rPDGF was removed by washing with 20 nM of Tris-HC1 (pH 7.4). After another washing with 20 nM of Tris-HC1 and 0.3 M NaCl (pH 7.4), dimeric rPDGF-B was eluted with 20 mM of Tris-HC1 and 0.7 M NaCl (pH 7.4).

Figure 4:
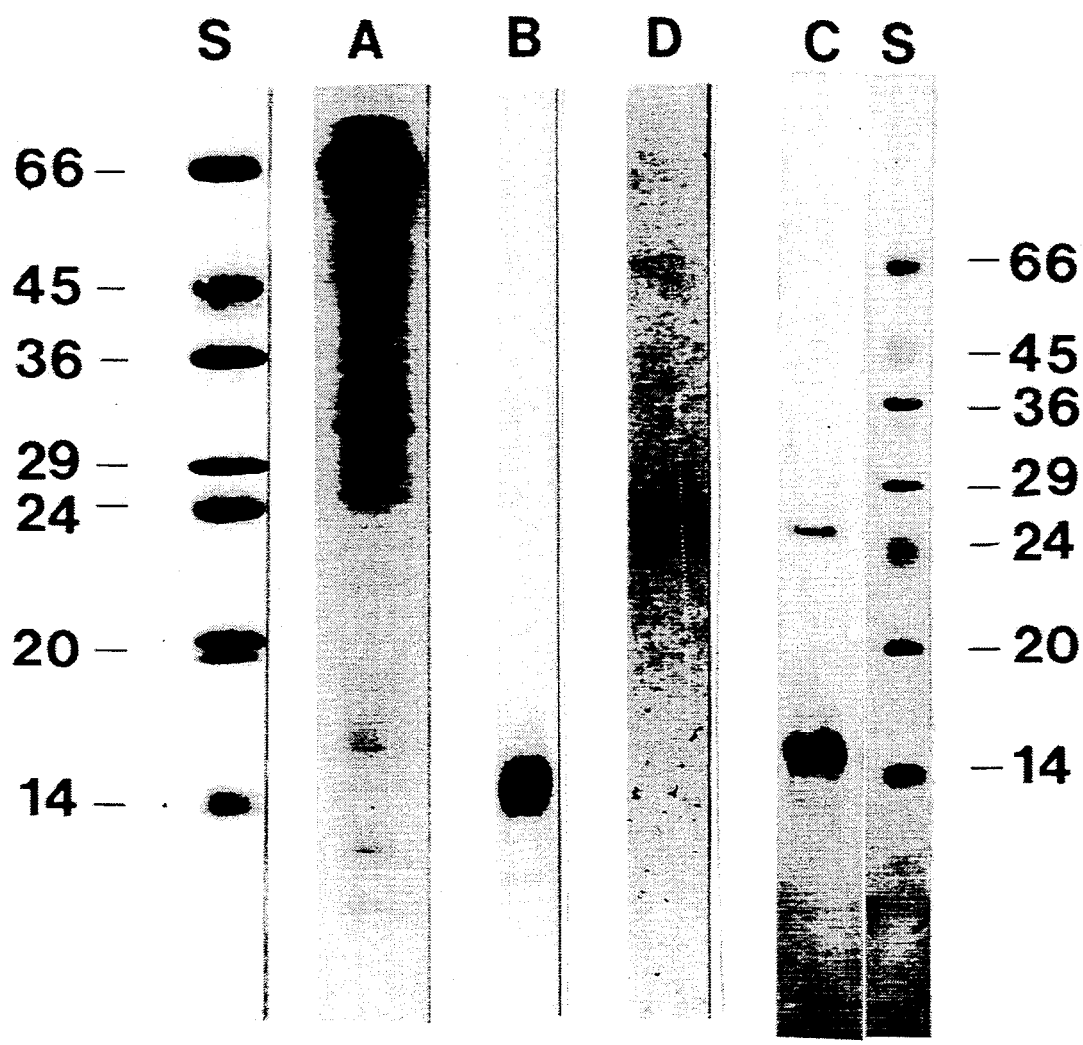

The yield after dimerization amounted to 0.5 to 0.7 mg of protein from i liter of culture. The protein was of high purity (after SDS gel electrophoresis) and semi-maximally stimulated the $^3$H-thymidine installation in mouse AKR 2B fibroblasts at a concentration of 1 to 2 ng/ml (FIGS. 4 and 5).

We claim:

1. An expression vector for producing PDGF-B comprising a DNA molecule having the nucleotide sequence of FIG. 3.

2. The *E. coli* host cell transformed with plasmid pE-pF14 which is deposited with the ATCC under accession number 68104.

3. A PDGF-B fusion protein comprising the amino acid sequence of FIG. 3.

* * * * *